(12) United States Patent
Burghardt et al.

(10) Patent No.: US 9,695,414 B2
(45) Date of Patent: Jul. 4, 2017

(54) SUSPENSION CONTAINER FOR BINDING PARTICLES FOR THE ISOLATION OF BIOLOGICAL MATERIAL

(71) Applicant: Roche Molecular Systems, Inc., Pleasanton, CA (US)

(72) Inventors: Geza Burghardt, Rotkreuz (CH); Willem Mulder, Lucerne (CH); Rolf Schneebeli, Mettmenstetten (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 40 days.

(21) Appl. No.: 14/617,372

(22) Filed: Feb. 9, 2015

(65) Prior Publication Data
US 2015/0152405 A1    Jun. 4, 2015

Related U.S. Application Data

(62) Division of application No. 13/239,144, filed on Sep. 21, 2011, now abandoned.

(51) Int. Cl.
| | |
|---|---|
| *B01L 3/00* | (2006.01) |
| *C12N 15/10* | (2006.01) |
| *B01F 15/00* | (2006.01) |
| *B03C 1/01* | (2006.01) |
| *B03C 1/28* | (2006.01) |

(Continued)

(52) U.S. Cl.
CPC ...... *C12N 15/1006* (2013.01); *B01F 11/0022* (2013.01); *B01F 15/00733* (2013.01); *B01F 15/00876* (2013.01); *B03C 1/01* (2013.01); *B03C 1/288* (2013.01); *G01N 1/405* (2013.01); *B01L 3/021* (2013.01); *B01L 3/50* (2013.01); *B01L 3/508* (2013.01); *B01L 7/52* (2013.01); *B01L 2200/0647* (2013.01); *B01L 2200/141* (2013.01); *B01L 2300/044* (2013.01); *B01L 2300/0672* (2013.01); *B01L 2300/0829* (2013.01); *B01L 2300/0832* (2013.01); *B01L 2400/043* (2013.01); *B01L 2400/0457* (2013.01); *B03C 2201/26* (2013.01)

(58) Field of Classification Search
None
See application file for complete search history.

(56) References Cited

U.S. PATENT DOCUMENTS

| | | |
|---|---|---|
| 4,695,430 A | 9/1987 | Coville et al. |
| 4,868,130 A | 9/1989 | Hargreaves |

(Continued)

FOREIGN PATENT DOCUMENTS

| | | |
|---|---|---|
| EP | 1614475 B1 | 5/2007 |
| GB | 2374413 A | 10/2002 |

(Continued)

*Primary Examiner* — Rebecca Martinez
(74) *Attorney, Agent, or Firm* — Pamela C. Ancona; M. Reza Savari

(57) ABSTRACT

A device, method and system is provided for binding particles for the separation and/or isolation of biological materials. In particular, a container is provided including a suspension of binding particles for the isolation of biological material, inner walls forming an elongate groove at the bottom of said container, and a cover having openings and/or being penetrable for a linear arrangement of multiple pipets or pipet tips, said openings being located above and parallel to said elongate groove.

4 Claims, 8 Drawing Sheets

(51) Int. Cl.
*B01F 11/00* (2006.01)
*G01N 1/40* (2006.01)
*B01L 3/02* (2006.01)
*B01L 7/00* (2006.01)

(56) References Cited

U.S. PATENT DOCUMENTS

| | | | |
|---|---|---|---|
| 4,986,965 | A | 1/1991 | Ushikubo |
| 5,230,427 | A | 7/1993 | Betts et al. |
| 6,254,826 | B1 | 7/2001 | Acosta et al. |
| 6,331,431 | B1 | 12/2001 | Glaser et al. |
| 6,461,034 | B1 | 10/2002 | Cleveland |
| 2005/0271550 | A1 | 12/2005 | Talmer et al. |
| 2007/0031963 | A1 | 2/2007 | Chang et al. |
| 2009/0134069 | A1 | 5/2009 | Handique |
| 2009/0148941 | A1 | 6/2009 | Florez et al. |
| 2010/0111772 | A1 | 5/2010 | Harfofelis |
| 2010/0119417 | A1 | 5/2010 | Motadel et al. |
| 2010/0163493 | A1* | 7/2010 | Hein .................. B03C 1/01 210/695 |
| 2011/0097240 | A1 | 4/2011 | Yamashita et al. |

FOREIGN PATENT DOCUMENTS

| | | |
|---|---|---|
| JP | 03292880 | 12/1991 |
| JP | 04208864 | 7/1992 |
| JP | 10316593 | 12/1998 |
| JP | 2005-10179 | 1/2005 |
| JP | 2011-59008 | 9/2009 |
| WO | 0137291 A1 | 5/2001 |
| WO | 03084664 A1 | 10/2003 |
| WO | 03084664 R1 | 10/2003 |
| WO | 2007055573 A1 | 5/2007 |
| WO | 2009024559 A1 | 2/2009 |
| WO | 2009151058 A1 | 12/2009 |

\* cited by examiner

SUSPENSION CONTAINER FOR BINDING PARTICLES FOR THE ISOLATION OF BIOLOGICAL MATERIAL

CROSS-REFERENCES TO RELATED APPLICATIONS

The present application is a divisional of application Ser. No. 13/239,144, filed on Sep. 21, 2011, the content of which is hereby incorporated herein by reference in its entirety.

FIELD OF THE INVENTION

The present invention belongs to the field of sample preparation for analytical purposes, particularly the separation and/or isolation of biological materials such as nucleic acids or proteins in or from complex mixtures. Within that field, the present invention relates to providing binding particles for the separation and/or isolation of biological materials.

BACKGROUND OF THE INVENTION

The isolation of biological materials such as nucleic acids or proteins from complex biological mixtures such as, e.g., clinical samples has been of considerable significance especially for diagnostic purposes.

Numerous different methods have been developed in the art, e.g., denaturing, precipitating and removing undesired components in a sample with subsequent precipitation and isolation of the analyte in question (for example alcohol-based precipitation of nucleic acids).

Another approach is the binding of the biological material to be isolated to a solid support material which may be provided, e.g., in the form of chromatographic columns.

For diagnostic purposes, and especially for the automated isolation of biological materials subject to subsequent medium- or high-throughput analysis, binding particles are often used. Such particles can have functionalized surfaces, i.e., they are often coated with antibodies, nucleic acid capture probes or the like, in order to bind the desired analyte. Alternatively, they may have unmodified surfaces such as glass surfaces particularly for the isolation of nucleic acids.

Such binding particles are, in connection with automated analyzers, often provided as a suspension in a container from which they are retrieved and dispensed with the help of pipetting tools. EP 1 614 475 suggests an approach for providing particles from a container for the isolation of biological material, disclosing the use of a container in the form of a plastic bottle agitated by a shaker, and the use of a pipet for distribution of the particles The present invention uses an improved approach displaying several advantages.

SUMMARY OF THE INVENTION

The present invention relates to providing binding particles for the separation and/or isolation of biological materials.

In particular, it relates to a suspension container (1), comprising a suspension of binding particles for the isolation of biological material, inner walls (2) forming an elongate groove (3) at the bottom of said container, and a cover (4) having openings (5) and/or being penetrable for a linear arrangement of multiple pipets or pipet tips, said openings being located above and parallel to said elongate groove.

Further provided is a method for pipetting a suspension of binding particles for the isolation of biological material, said method comprising the automated steps of:

a. agitating a container (1) containing said suspension of binding particles, said container comprising inner walls (2) forming an elongate groove (3) at the bottom of said container, said container further comprising a cover (4) having openings (5) and/or being penetrable for a linear arrangement of multiple pipets or pipet tips;

b. introducing into said suspension said linear arrangement of multiple pipets or pipet tips through said openings and/or penetrable cover; and c. aspirating at least a portion of said suspension with a linear arrangement of multiple pipets or pipet tips and releasing the aspirated suspension or a portion thereof into multiple vessels.

Also provided by the invention is an analytical system for providing binding particles for the isolation of biological material, said analytical system comprising a linear arrangement of multiple pipets or pipet tips, a container containing a suspension of binding particles for binding said biological material, said container comprising an elongate cavity at its bottom, said container further comprising a cover, said cover having openings and/or being penetrable for said linear arrangement of multiple pipets or pipet tips, and a shaker for agitating said container and suspending said binding particles.

DETAILED DESCRIPTION OF THE INVENTION

Figure 1:
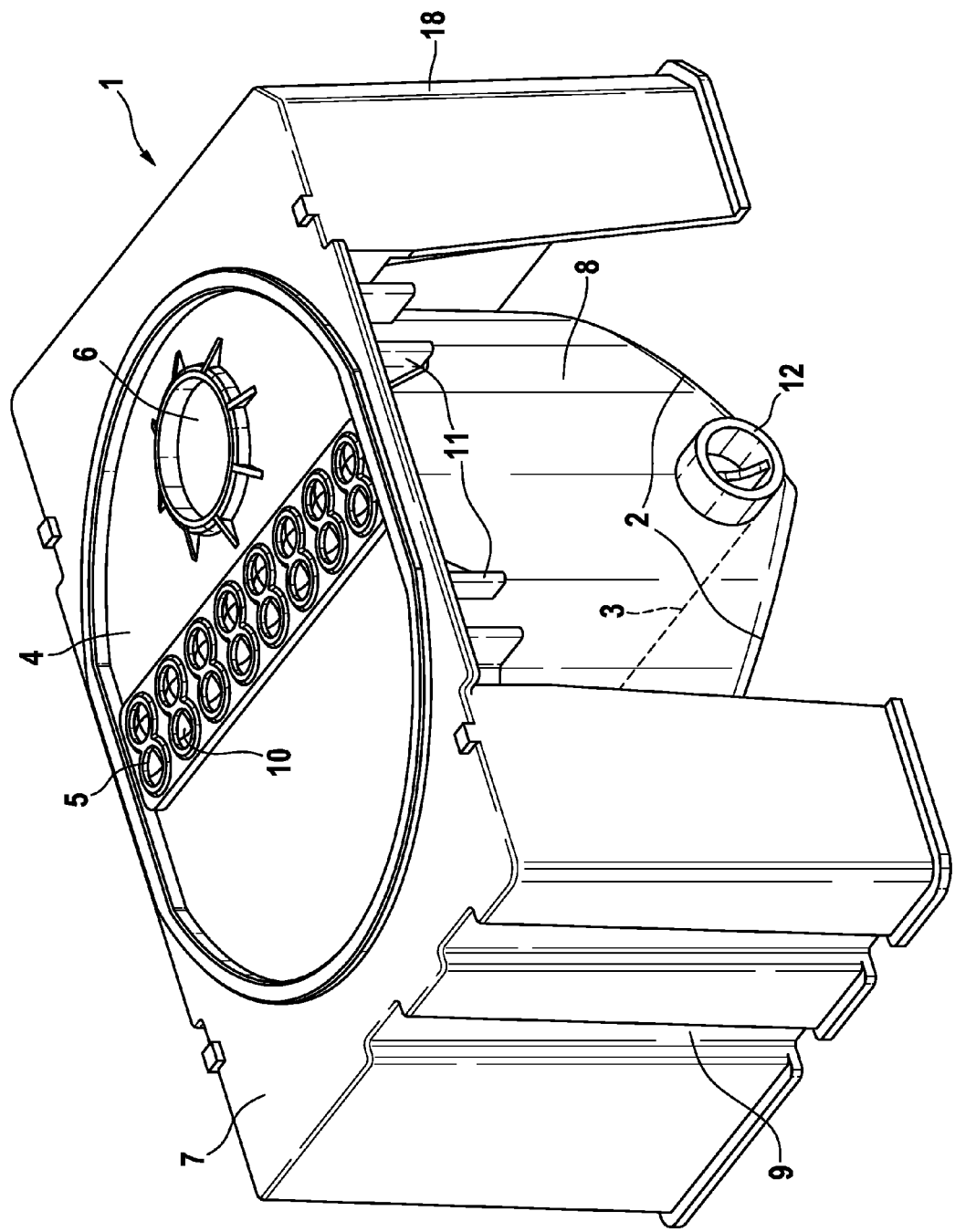
FIG. 1 shows a perspective view of a suspension container with cover from above.

The present invention relates to providing binding particles for the separation and/or isolation of biological materials.

In particular, a suspension container, a method and an analytical system for the purpose mentioned above are provided.

Among the advantages that certain embodiments of the present invention provide are, for example, the following:
  homogeneous distribution of binding particles from a
    container to vessels for downstream processing, particularly isolation of biological material
  parallelization of the provision of binding particles, thus
    facilitating a high throughput especially for automated systems
  avoiding contamination
  increasing stability of the suspension
  avoiding loss of suspension material due to agitation of
    the container quantitative retrieval of the suspension from its container flexibility in throughput individual dispense of binding particles.

It is set out in the following which embodiments bring about which specific advantages.

In a first aspect, the invention brings about certain advantages mentioned above by providing a suspension container, comprising:

a suspension of binding particles for the isolation of biological material inner walls forming an elongate groove at the bottom of said container a cover having openings and/or being penetrable for a linear arrangement of multiple pipets or pipet tips, said openings being located above and parallel to said elongate groove.

The suspension container according to the invention ensures a reduced risk of contamination due to the presence of a cover protecting the suspension of binding particles from potential contaminating material.

In the context of isolating biological material for subsequent analysis, contamination of the sample often leads to severe consequences, in particular with respect to clinical samples. Especially in the case of material that becomes amplified during analysis (e.g., nucleic acids), already very little amounts of contamination can lead to false positive results in qualitative assays, or to overestimation of a titer in quantitative assays. Both problems may have a significant impact on diagnosis or the respective treatment of diseases.

In addition, the introduction of inhibitory substances like, e.g., certain proteins can impede the analytical experiments such that no results are obtained at all.

Besides, substances could be introduced that decrease the stability of the suspension, or have an influence on its physicochemical properties such as concentration, ionic strength etc.

Furthermore, the use of a cover is considerably advantageous when the suspension container is agitated. Agitation of the suspension of binding particles is often carried out in order to resuspend particles. Whenever the container is not moving, sedimentation of the particles takes place due to the influence of gravity. It is, however, important to provide the suspension of binding particles in a homogeneous manner, so that in multiple withdrawals of suspension an essentially equal number of binding particles is retrieved when withdrawing equal volumes of suspension. As a consequence, the concentration throughout the suspension must be essentially constant during the various events of withdrawal.

In the prior art, containers with a suspension of binding particles for the isolation of biological material are, e.g., agitated on a shaker or mixed with a stirrer. While a stirrer is another potential source of contamination, agitation introduces the problem of losing suspension due to spilling. On the other hand, in automated solutions, placing a cover on the container is connected with the problem that withdrawal of the suspension should be enabled in a manner as easy as possible. For example, removal of the cover prior to every withdrawal would require an additional step in a method for providing a suspension of binding particles, and opening the container also increases the risk of contamination.

Thus, one of the advantages of the suspension container according to the invention comprises a cover having openings and/or being penetrable for a linear arrangement of multiple pipets or pipet tips. This way, the risk of both spilling and contamination is considerably reduced while the cover need not be removed in order to withdraw the suspension of binding particles. The suspension container can be used for providing suspension until it is empty without the need to open it.

Since the cover has openings and/or is penetrable for a linear arrangement of multiple pipets or pipet tips, it can be advantageously used for parallelization of the provision of a suspension of binding particles. Using multiple pipets enables the artisan to dispend the suspension of binding particles into multiple vessels at the same time. Particularly in the context of automated solutions, a medium to high throughput of samples is often desired. As an example, diagnostic tests of clinical samples such as blood screening in an in vitro diagnostic context, e.g., for blood banks, require the analysis of a high number of samples within a limited period of time. Also, laboratories serving as centralized facilities for the analysis of clinical samples from several hospitals need to quickly provide analytical results. The latter are often important for a treatment following the analysis of the sample. Parallelization can lead to a decrease in the number of single test runs to make a diagnosis, and potentially shorter hospital stays (e.g., if a diagnosis can be provided sooner, patients requiring antimicrobial therapy will receive it sooner and thus recover earlier). Moreover, providing a negative result sooner can avoid the overprescription of antibiotics.

In embodiments where the cover has openings, these are located above and parallel to the elongate groove that is formed at the bottom of the container by its inner walls.

In the sense of the invention, an "opening" as used in connection with the cover is an aperture allowing a pipet tip to be introduced into the container and thus withdrawing the suspension without removing the cover. In preferred embodiment of the invention, said openings are holes. Preferably, said holes are round-shaped, while they can have any other geometrical shape allowing the passage of the linear arrangement of pipets or pipet tips.

"Penetrable" means closed, but still able to be penetrated. More specifically, with regard to the cover of the suspension container, "penetrable" means that the cover is in principle closed, but still allows the passage of the linear arrangement of pipets or pipet tips. As an example, the cover can be a septum made of rubber or a rubber-like material that can be pierced by a pipetting needle. A septum used in the context of the invention is made of essentially flexible material. Preferably, the cover being penetrable for a linear arrangement of pipets or pipet tips is a septum. Preferably, the cover is air-proof. An air-proof cover has the advantage of efficiently preventing introduction of contaminating material into the container.

The groove mentioned above facilitates the complete withdrawal of suspension from the container, as residual volumes gather in the groove. According to the invention, the groove's elongate form is adapted to the linear arrangement of pipets or pipet tips. The latter can thus enter the container through the openings and aspirate the residual volume from the groove. Thereby it is ensured that only little residual volume remains in the container and is discarded without having been used. Especially in an automated system including a cover through which pipets or their corresponding tips have to be introduced in the container, usually in a straight vertical line, this would be more difficult without the presence of such an elongate groove. For example, a residual volume of suspension could remain on parts of the bottom of the container that are not reached by the pipets, such that they would be discarded without having been used. Furthermore, when the container is agitated in order to achieve or maintain a homogeneous distribution of the binding particles, "dead corners" may result in a design without an elongate groove as used in the present invention. This means that, e.g., in a container with a flat bottom and corners at the borders of bottom and side walls, that are, e.g., orthogonal to each other, binding particles may be kept in said corners and are thus not reached by the stream caused by agitation of the container. Such a phenomenon may lead to an inhomogeneous distribution of the binding particles and thus varying concentrations of the particles withdrawn by pipetting. The larger the container, the more likely and the more severe the problems set out above become.

The elongate groove can, e.g., be caused by a parabolic or otherwise concave arrangement of the inner walls of the container. Said groove is preferably essentially in the center of the bottom. This way, no edges or corners are created within the container.

The elongate groove can also be formed as a result of two inner walls bordering each other at a certain angle. This embodiment can be advantageous for production of the container, and the relatively sharp-edged groove can serve as a well-defined cavity for the collection of residual suspension volumes in which the pipets or pipet tips can be introduced for efficient withdrawal of said residual suspension volumes. Furthermore, the relatively sharp-edged groove created by the two inner walls inclined in an angle to each other introduces a baffle-like structure which can be advantageous for providing a homogeneous distribution of the binding particles within the suspension. Baffles are known in the art to contribute to a homogeneous distribution in suspensions in agitated containers such as Erlenmeyer flasks.

Thus, a preferred aspect of the invention is the suspension container described above, wherein said inner walls are inclined in an angle to each other and thereby form said elongate groove.

The "angle" (denoted "$\alpha$" in FIG. 3) is larger than 0° and smaller than 180°. If said walls together formed an entirely flat bottom, the angle would be 180°, resulting in the absence of a groove. If the angle was 0°, no bottom at all could be formed. Preferably, the angle is between 90° and 180°.

In the context of the invention, when pipets form the linear arrangement of pipets or pipet tips, the pipets are preferably pipetting needles. Such needles are often used in connection with automated diagnostic systems, for example because of their advantageously small diameter and the precision with which they can be handled, e.g., by a robotic arm. If the linear arrangement of pipets or pipet tips is formed by pipet tips, said pipet tips also need to be fixed to pipets in order to serve their purpose of pipetting the suspension comprised by the container. In this embodiment, said pipet tips are preferably disposable pipet tips into which said suspension is aspirated and from which it is dispensed again. Such a pipet tip can be used several times before being discarded and replaced. Often, but not necessarily, such pipet tips are made of plastic. Disposable pipet tips are generally known in the art.

A "linear arrangement" means that the pipets or pipet tips are arranged in a row, preferably in a straight line. The arrangement comprises a bearing to which the corresponding pipets are fixed. Preferably, the bearing is also adapted to manipulate and move the linear arrangement of pipets or pipet tips in all dimensions, i.e., on an x, y and z-axis. Preferably, said bearing is a robotic arm, preferably adapted to facilitate aspirating the suspension from the container and dispensing it into receptacles.

As mentioned above, the invention provides the opportunity to achieve a high analytical sample throughput and quick results by parallelization. It is thus preferable that the linear arrangement of pipets or pipet tips comprises at least a certain number of pipets or pipet tips, preferably at least four, more preferably at least eight, most preferably eight pipets or pipet tips.

"Binding particles for the isolation of biological material" are a solid phase on which biological material can be immobilized. The particles can comprise different materials and shapes. For example, particles such as beads or fleece with a diameter in the nano-, micro or millimeter range can be suitable for binding biological material. "Biological material", in the sense of the invention, comprises all kinds of biological molecules, for example proteins or nucleic acids, but also other molecules occurring in nature or being derivatives or synthetic analogues or variants thereof. Furthermore, the term "biological material" comprises viruses and eukaryotic and prokaryotic cells. Often such cells or viruses are bound to said binding particles via biomolecules, especially proteins, that are present in their respective cell membrane or capsid. For the purpose of binding biological material, it is often advantageous to modify the surface of said binding particles by coating them with biomolecules with a specific or non-specific affinity to the biological material to be bound. As an example, such a coating can comprise streptavidin which specifically binds to biotin. The latter is often chemically attached to biomolecules in order to bind them to streptavidin-comprising surfaces such as surface of respectively modified binding particles. For the same purpose, interactions between histidine tags and nickel or between antibodies and their antigens or epitopes can be exploited. In the context of nucleic acids as a biological material to be bound, so-called capture probes can be advantageously used. These capture probes are nucleic acids themselves, mostly oligonucleotides, often with a length of about 15 to 25 nucleotides, that bind to essentially complementary nucleic acid sequences by Watson-Crick base-pairing. Methods comprising binding particles coated with specific binders have the advantage that a specific biological material, such as a specific protein or nucleic acid, can be isolated while other proteins or nucleic acids are not bound. This can contribute to the isolation of such a specific biological material for analytical purposes. The skilled artisan understands that there is a variety of interactions between biological material and specific coatings of binding particles that can be used within the spirit of the invention. Methods for coating such binding particles are described in the prior art.

Particularly interesting for nucleic acid extraction purposes is their adsorption to a glass surface although other surfaces are possible. Many procedures for isolating nucleic acids from their natural environment have been proposed in recent years by the use of their binding behavior to glass surfaces. If unmodified nucleic acids are the target, a direct binding of the nucleic acids to a material with a silica surface is preferred because, among other reasons, the nucleic acids do not have to be modified, and even native nucleic acids can be bound. These processes are described in detail by various documents, e.g., in Vogelstein B. et al., Proc. Natl. Acad. USA 76 (1979).

In the sense of the invention, the terms "isolation", "purification" or "extraction" of biological material relate to the following: Before biological material like nucleic acids may be analyzed in a diagnostic assay, e.g., by amplification, they typically have to be purified, isolated or extracted from biological samples containing complex mixtures of different components. Often, for the first steps, processes are used which allow the enrichment of the material. To release the contents of cells or viral particles, they may be treated with enzymes or with chemicals to dissolve, degrade or denature the cellular walls or viral particles. This process is commonly referred to as lysis. The resulting solution containing such lysed material is referred to as lysate. A problem often encountered during lysis is that other enzymes degrading the component of interest, e.g., deoxyribonucleases or ribonucleases degrading nucleic acids, come into contact with the component of interest during the lysis procedure. These degrading enzymes may also be present outside the cells or may have been spatially separated in different cellular compartments prior to lysis. As the lysis takes place, the component of interest becomes exposed to said degrading enzymes. Other components released during this process may, e.g., be endotoxins belonging to the family of lipopolysaccharides which are toxic to cells and can cause problems for products intended to be used in human or animal therapy.

There is a variety of means to tackle the above-mentioned problem. It is common to use chaotropic agents such as guanidinium thiocyanate or anionic, cationic, zwitterionic or non-ionic detergents when nucleic acids are intended to be set free. It is also an advantage to use proteases which rapidly degrade the previously described enzymes or unwanted proteins. However, this may produce another problem as said substances or enzymes can interfere with reagents or components in subsequent steps.

Enzymes which can be advantageously used in such lysis or sample preparation processes mentioned above are enzymes which cleave the amide linkages in protein substrates and which are classified as proteases, or (interchangeably) peptidases. Especially advantageous for the use in lysis or sample preparation processes mentioned above is the enzyme esperase, a robust protease that retains its activity at both high alkalinity and at high temperatures (EP 1 201 753).

In the sample preparation steps following the lysis step, the component of interest is further enriched, preferably by using the binding particles comprised by the suspension container according to the invention.

For instance, a procedure for binding nucleic acids entails the selective binding of nucleic acids to glass surfaces of binding particles in chaotropic salt solutions and separating the nucleic acids from contaminants such as agarose, proteins or cell residue. To separate the glass particles from the contaminants, the particles may be either centrifuged or fluids are drawn through glass fiber filters. The use of magnetic particles to immobilize nucleic acids after precipitation by adding salt and ethanol is more advantageous and described, e.g., in Alderton R. P. et al., S., Anal. Biochem. 201 (1992) 166-169 and PCT GB 91/00212. Magnetic, porous glass is also available on the market that contains magnetic particles in a porous, particular glass matrix and is covered with a layer containing streptavidin. This product can be used to isolate biological materials, e.g., proteins or nucleic acids, if they are modified in a complex preparation step so that they bind covalently to biotin. Magnetizable particular adsorbents proved to be very efficient and suitable for automatic sample preparation. Ferrimagnetic and ferromagnetic as well as superparamagnetic pigments are used for this purpose.

A preferred aspect of the invention is the suspension container described above, wherein said binding particles comprise nucleic acid binding particles. More preferably, they comprise magnetic glass particles. Even more preferably, they comprise magnetic glass particles with an unmodified glass surface. Also preferably, they comprise magnetic glass particles produced by the sol-gel method. Most preferably, they comprise magnetic glass particles produced by the sol-gel method and having an unmodified glass surface. In a preferred embodiment, said binding particles are nucleic acid binding particles, preferably magnetic particles and/or glass particles. In a more preferred embodiment, said binding particles are magnetic glass particles, preferably produced by the sol-gel method and/or having an unmodified glass surface.

The most preferred magnetic particles and methods using them are those described in WO 01/37291. In brief, these magnetic glass particles are a solid dispersion of small magnetic cores in glass. They are furthermore comparatively small and substantially spherical. The non-magnetic fine content of a composition of the magnetic glass particles is very low because of the method of their preparation. This has the effect that suspensions of these magnetic glass sediment slowly and can therefore be advantageously used for processes in molecular biology which can be automated.

A "glass" according to the present invention is understood to be an essentially amorphous material that contains silicon. Glass can contain other materials such as, for example, $B_2O_3$ (0-30%), $Al_2O_3$ (0-20%), CaO (0-20%), BaO (0-10%), $K_2O$ (0-20%), $Na_2O$ (0-20%), MgO (0-18%), $Pb_2O_3$ (0-15%). Glass can also contain a smaller percentage (0-5%) of a number of other oxides such as $Mn_2O_3$, $TiO_2$, $As_2O_3$, $Fe_2O_3$, CuO, CoO, etc.

Especially preferred are glasses that are formed using the gel sol process described in WO 96/41811 and then dried and compressed.

Particularly useful for the nucleic acid isolation in the context of the invention is the method according to R. Boom et al. (J Clin Microbiol. 28 (1990), 495-503).

After the purification or isolation of the nucleic acids potentially including a specific target nucleic acid from their natural surroundings, the nucleic acids or the specific target nucleic acid may be detected.

Optionally, prior to detection, they may be amplified by techniques such as the Polymerase Chain Reaction (PCR, described, e.g., in U.S. Pat. No. 4,683,202). PCR typically employs two or more oligonucleotide primers that bind to a selected nucleic acid template (e.g., DNA or RNA).

Nucleic acid amplification reactions apart from PCR comprise the Ligase Chain Reaction (LCR; Wu D. Y. and Wallace R. B., Genomics 4 (1989) 560-69; and Barany F., Proc. Natl. Acad. Sci. USA 88 (1991)189-193); Polymerase Ligase Chain Reaction (Barany F., PCR Methods and Applic. 1 (1991) 5-16); Gap-LCR (WO 90/01069); Repair Chain Reaction (EP 0439182 A2), 3SR (Kwoh D. Y. et al., Proc. Natl. Acad. Sci. USA 86 (1989) 1173-1177; Guatelli J. C., et al., Proc. Natl. Acad. Sci. USA 87 (1990) 1874-1878; WO 92/08808), and NASBA (U.S. Pat. No. 5,130,238). Further, there are strand displacement amplification (SDA), transcription mediated amplification (TMA), and Qβ-amplification (for a review see, e.g., Whelen A. C. and Persing D. H., Annu. Rev. Microbiol. 50 (1996) 349-373; Abramson R. D. and Myers T. W., Curr Opin Biotechnol 4 (1993) 41-47).

Suitable nucleic acid detection methods are known to the expert in the field and are described in standard textbooks as Sambrook J. et al., Molecular Cloning: A Laboratory Manual, Cold Spring Harbor Laboratory Press, Cold Spring Harbor, N.Y., 1989 and Ausubel F. et al.: Current Protocols in Molecular Biology 1987, J. Wiley and Sons, NY. There may be also further purification steps before the nucleic acid detection step is carried out as, e.g., a precipitation step. The detection methods may include but are not limited to the binding or intercalating of specific dyes as ethidium bromide which intercalates into the double-stranded DNA and changes its fluorescence thereafter. The purified nucleic acid may also be separated by electrophoretic methods optionally after a restriction digest and visualized thereafter. There are also probe-based assays which exploit the oligonucleotide hybridization to specific sequences and subsequent detection of the hybrid. It is also possible to sequence the nucleic acid after further steps known to the expert in the field. A useful template-dependent nucleic acid polymerase is the ZO5 DNA polymerase and mutations thereof. Other template-dependent nucleic acid polymerases comprise, e.g., Taq polymerase and Tth Polymerase.

In a preferred embodiment of the invention, the suspension container described supra further comprises one or more elements selected from the group of:

fill-openings for filling the suspension of binding particles into the container a removable foil sealing the cover.

While, without leaving the scope of the invention, refilling the container is possible, the suspension container according to the invention is preferably disposable, i.e., it is used until no more suspension is present within, and then the container is discarded. This bears the advantage that no contamination can be introduced by refilling the container.

For primary filling of the container with the suspension of binding particles for the isolation of biological material, it is preferable that fill-openings are present in the cover. Said fill-openings can have any geometrical shape. Preferably, the fill-openings are wider than the openings for a linear arrangement of multiple pipets or pipet tips. In a preferred embodiment, the fill-openings are used only once for filling the container, and then they are sealed. Preferably, they remain sealed until the container is discarded. Also preferably, they are sealed in a sterile manner. Different materials can be used to seal said fill-openings, e.g., plastics, metal or others. Preferably, the fill-openings are sealed with a sterile foil.

Further in connection with the avoidance of contamination, a preferred aspect of the invention is the suspension container described above, wherein said cover has openings, said openings being covered by a penetrable septum. In this embodiment, the advantages of openings and a penetrable septum are combined. The openings taken alone provide, e.g., the advantage of allowing pipets or pipet tips to pass through an otherwise closed cover while largely excluding sources of contamination, especially in the preferred embodiment when said openings are not significantly larger in diameter than necessary to let the pipets or pipet tips pass. Furthermore, they can be easily introduced into a cover, the cover providing a stable barrier between the interior and the exterior of the container. The septum, on the other hand, is able to essentially seal any opening such as the aperture of the container according to the invention. Since a septum as used in the invention is made of essentially flexible material such as, e.g., rubber or other suitable materials, openings in a septum are only created when the linear arrangement of pipets or pipet tips penetrates said septum, while after such penetration the created openings essentially close again. In combination, a cover comprising openings provides a stable barrier on top of the container according to the invention while still allowing the linear arrangement of pipets or pipet tips to be introduced into the container, whereas an additional septum contributes to a reduced risk of contamination by essentially sealing said openings in the cover but being penetrable for said pipets or pipet tips. Preferably, said septum is fixed above or underneath said openings and seals them before and preferably also after introduction of the linear arrangements of pipets or pipet tips. In a further preferred embodiment, the cover comprising openings consists of two layers of a rigid material such as preferably plastic, and a septum sandwiched in between said layers of a rigid material, thereby sealing said openings. The septum is preferably made of rubber or a rubber-like material, such that it essentially closes the hole after the pipets or pipet tips are removed from the openings and thus the septum. "Essentially closes" in this context means that the penetrated septum is preferably still suited to prevent the introduction of contamination. Preferably, it is still air-proof at atmospheric pressure.

Since it is important to provide the suspension container according to the invention in a manner that contamination is avoided as far as possible, it is preferable that it comprises a removable foil sealing the cover. Said foil is preferably removed prior to the first use of the container in order to allow the linear arrangement of pipets or pipet tips to be introduced into the container and thus the suspension. Preferably, the foil is then discarded. Alternatively, said foil can remain on or underneath the cover if it is penetrable for the linear arrangement of pipets or pipet tips.

In the context of packaging the suspension container, e.g., for transporting and providing it to its user, it can be provided in a sterile and biological material-free airproof plastic packaging, while other packaging materials may also be suitable. Preferably, such packaging allows the artisan to insert the container into an automated system such as an apparatus without coming into physical contact with the suspension of binding particles within the container.

Another preferred aspect of the invention is the suspension container described above, wherein said container is adapted to hold a volume of at least 100 ml, preferably of 100 to 500 ml, more preferably of 150 to 300 ml.

Especially when aiming at automated high-throughput solutions with parallelization of sample preparation and analytical reactions, it is preferable to use a suspension container with a comparatively large quantity of suspension of binding particles. Such a container can be used for providing a suspension of binding particles for a large number of experiments before it has to be discarded and eventually replaced. It is preferable not to replace a container very frequently, since, e.g., opening and closing an apparatus mostly introduces a risk of contamination.

Using a container with a comparatively large volume as described supra includes the challenge that only little residual volumes should remain unused in the container despite the large inner surface. This problem is solved by the container according to the invention by the elongate groove in conjunction with the openings and/or penetrable cover as described above.

Also, the problem of spilling and thus loss of suspension when agitating the container is solved by the invention through the cover comprised by the container according to the invention. This is also a problem occurring more frequently when using containers with a higher volume.

For agitation, the suspension container is preferably placed on a shaker. Laboratory shakers are known in the art and can fulfill a variety of movements suitable for resuspending potentially sedimented binding particles. In order to provide a stable connection between container and shaker during agitation, a preferred aspect of the invention is the suspension container described above, wherein said container comprises one or more fastenings for reversibly fixing the container to a shaker. Said fastenings can be attached to the suspension container during or after its production.

A container according to the invention can be made from different materials. If, for example, the container is made of plastic, its production process preferably includes injection molding, such that said fastenings may be introduced during the production steps. The container is preferably made of polypropylene. In a production method useful in the context of the present invention, the container is made in a two-step procedure. At first, the lower part of the container, i.e., the tray later containing the suspension, is made via a one-component injection molding process using polypropylene and a suitable molding tool. In another step, the cover is manufactured from two components, wherein first the basic form is made of polypropylene by injection molding, then the material forming a septum (e.g., rubber) is added to and combined with the cover.

With regard to filling the container with the suspension of binding particles, it is preferred to make the suspension by first weighing the solid material and adding a predefined amount to a suitable container which is preferably already the container according to the invention, and then adding a predefined volume of the respective liquid matrix. This way, mostly even amounts of liquid and particles and thus mostly uniform suspensions can be provided within different containers. Furthermore, adding the particles prior to the liquid first has the advantage that clumping is avoided, which is more likely to occur if the particles are added to the liquid. Preparing the solution within the container of the invention instead of pre-creating the suspension and then transferring the latter as such to the container bears yet another advantage: In case the suspension is added as such, it has to kept homogeneous, e.g., by agitating, before and/or while it is transferred to the container, in order to provide mostly uniform suspensions in different containers. This can be avoided if the filling is performed by first adding the binding particles as described above.

Preferably, the shaker comprises elements such as indentations or recesses corresponding to the fastenings present on the container in order to permit a stable fixture. Said fixture can preferably be reopened. Since the container according to the invention is preferably disposable, it is advantageous if it can be removed from the shaker after being empty, so it can be replaced by a new suspension container filled with a suspension of binding particles.

In a further preferred aspect of the invention the footprint of the suspension container described above is oval-shaped. This shape facilitates achieving a homogeneous particle distribution when the container is agitated. Furthermore, collecting residual volumes of suspension and also potentially sedimented binding particles in the elongate groove at the bottom of the container is facilitated by said oval-shaped footprint. Other geometrical shapes serving these purposes may be employed, such as, e.g., an essentially round-shaped footprint. The combination of a footprint as described above with said elongate groove and said cover is particularly advantageous for providing a homogeneous distribution of binding particles.

Another preferred aspect of the invention is a method for pipetting a suspension of binding particles for the isolation of biological material, said method comprising the automated steps of:
   a. agitating a container (1) containing said suspension of binding particles, said container comprising inner walls (2) forming an elongate groove (3) at the bottom of said container, said container further comprising a cover (4) having openings (5) and/or being penetrable for a linear arrangement of multiple pipets or pipet tips
   b. introducing into said suspension said linear arrangement of multiple pipets or pipet tips through said openings and/or penetrable cover
   c. aspirating at least a portion of said suspension with a linear arrangement of multiple pipets or pipet tips and releasing the aspirated suspension or a portion thereof into multiple vessels.

In the context of said method, it is preferable that the agitation is stopped before step b. This way, the linear arrangement of multiple pipets or pipet tips has a better access to the suspension, and moving parts of the container cannot damage them. Alternatively, the openings in the cover of the container are wide enough to allow pipetting through the cover during agitation, whereby the linear arrangement of multiple pipets or pipet tips is not touched by the rims of the opening.

When aspirating suspension, it is preferable that enough suspension is aspirated at a time to allow for multiple pipetting into several reaction vessels. Preferably, each pipet or pipet tip releases the aspirated suspension in multiple portions and thus pipetting events. This embodiment contributes to parallelization of the method.

A preferred aspect of the invention is the method described above, wherein in step c. said linear arrangement of multiple pipets or pipet tips simultaneously releases said suspension into said multiple vessels. This means that all pipets or pipet tips belonging to said linear arrangement release the aspirated suspension or a portion thereof at the same time. This way, e.g., multiple wells of a multi- or deepwell plate can be filled with suspension at the same time.

In another preferred embodiment, the invention concerns the method described above, wherein in step c. said linear arrangement of multiple pipets or pipet tips individually releases said suspension into said multiple vessels by independently manipulating one or more of said multiple pipets or pipet tips of said linear arrangement.

This way, e.g., only selected wells of a multi- or deepwell plate can be filled with suspension at the same time. Such pipetting in a coordinated manner can be controlled by a controlling unit. A control unit may comprise software for ensuring that the different components of an analytical system work and interact correctly and with the correct timing, e.g., moving components such as the pipets or pipet tips belonging to said linear arrangement in a coordinated manner. The control unit may also comprise a processor running a real-time operating system (RTOS), which is a multitasking operating system intended for real-time applications. In other words the system processor is capable of managing real-time constraints, i.e., operational deadlines from event to system response regardless of system load. It controls in real time that different units within the system operate and respond correctly according to given instructions.

A corresponding analytical system is also provided by the invention. Thus, another preferred aspect is an analytical system for providing binding particles for the isolation of biological material, said analytical system comprising:
   a linear arrangement of multiple pipets or pipet tips
   a container containing a suspension of binding particles for binding said biological material, said container comprising an elongate cavity at its bottom, said container further comprising a cover, said cover having openings and/or being penetrable for said linear arrangement of multiple pipets or pipet tips
   a shaker for agitating said container and suspending said binding particles.

In said analytical system, the components interact in a way as described supra for the container and the method according to the invention.

Another preferred aspect of the invention is the analytical system described above, wherein the system further comprises a plurality of vessels for receiving said suspension of binding particles from said linear arrangement of multiple pipets or pipet tips.

It is preferable that said multiple pipets or pipet tips release the aspirated suspension into multiple vessels instead of a single vessel, in order to facilitate parallelization of the provision of suspension of binding particles. These multiple vessels may comprise, e.g., test reagents and/or different samples from different sources, while all vessels make use of the same suspension of binding particles for the isolation of the biological material to be analyzed.

In this context, it is preferable that said linear arrangement of pipets or pipet tips comprises at least a certain number of pipets or pipet tips, preferably at least four, more preferably at least eight, most preferably eight pipets or pipet tips.

Another preferred aspect of the invention is the analytical system described above, said system further comprising a separation station for the isolation of said biological material with said binding particles.

A "separation station" is a device or a component of an analytical system allowing for the isolation of the binding particles from the other material present in the fluid sample. Such a separation station can, e.g., comprise, but is not limited to, a centrifuge, a rack with filter tubes, a magnet, or other suitable components. In a preferred embodiment of the invention, the separation station comprises one or more magnets. Preferably, one or more magnets are used for the separation of magnetic particles, preferably magnetic glass particles. If, for example, the fluid sample and the binding particles are combined together in the wells of a multiwell plate, then one or more magnets comprised by the separation station can, e.g., be contacted with the fluid sample itself by introducing the magnets into the wells, or said one or more magnets can be brought close to the outer walls of the wells in order to attract the magnetic particles and subsequently separate them from the surrounding liquid.

In a preferred embodiment, the separation station comprises a multiwell plate comprising vessels with an opening at the top surface of the multiwell plate and a closed bottom. The vessels comprise an upper part, a center part and a bottom part, wherein the upper part is joined to the top surface of the multiwell plate and preferably comprises two longer and two shorter sides. The center part preferably has a substantially rectangular cross-section with two longer sides, wherein said vessels are preferably aligned in rows. A continuous space is preferably located between two adjacent rows for selectively contacting at least one magnet mounted on a fixture with the side walls in at least two Z-positions. The separation station preferably further comprises a magnetic separation station comprising at least one fixture. The fixture preferably comprises at least one magnet generating a magnetic field. A moving mechanism is preferably present which vertically moves said at least one fixture comprising at least one magnet at least between first and second positions with respect to the vessels of the multiwell plate. Preferably, said at least two Z-positions of the vessels comprise the side walls and the bottom part of said vessels. The magnetic field of said at least one magnet preferably draws the magnetic particles to an inner surface of the vessel adjacent to said at least one magnet when said at least one magnet is in said first position. The effect of said magnetic field is less when said at least one magnet is in said second position than when said at least one magnet is in said first position. Preferably, the fixture comprising said at least one magnet comprises a frame. The separation station preferably comprises a frame to receive the multiwell plate, and latch-clips to attach the multiwell plate. Preferably, the separation station comprises two types of magnets. A second preferred embodiment comprises a spring which exerts a pressure on the frame comprising the magnets such that the magnets are pressed against the vessels of the multiwell plate. The first magnets are preferably constructed and arranged to interact with vessels of a multiwell plate for exerting a magnetic field on a large volume of liquid comprising magnetic particles held in said vessels. Said second magnets are preferably constructed and arranged to interact with vessels of a multiwell plate for exerting a magnetic field on a small volume of liquid comprising magnetic particles held in said vessels. Said first and second magnets can be preferably moved to different Z-positions.

A yet further preferred aspect of the invention is the analytical system described above, said system further comprising one or more elements selected from the group consisting of:

a reaction module containing the components of a chemical and/or biochemical reaction a detection module for detecting signals evoked by an analyte a storage module for reagents and/or disposables.

A "reaction module" is a module in which a reaction such as Polymerase Chain Reaction (PCR) or hybridization of antibodies for the analysis of the sample or a specific analyte therein takes place. It can, e.g., comprise a variety of vessels like tubes or plates. The outer limits or walls of such vessels are chemically inert such that they do not interfere with the analytical reaction taking place within. If the material to be analyzed is nucleic acids, there are various methods applicable in this context, one very significant method being the Polymerase Chain Reaction mentioned above.

A "detection module" is a module in which the detection of a signal, preferably the signal evoked by an analyte or a control, is performed. A detection module can, e.g., be an optical detection unit for detecting the result or the effect of the analysis procedure. An optical detection unit may comprise a light source, e.g., a xenon lamp, optics such as mirrors, lenses, optical filters, fiber optics for guiding and filtering the light, one or more reference channels, or a CCD camera.

A "storage module" stores the necessary reagents to bring about a chemical or biological reaction important for analysis of the sample in question. It can also contain further components useful for the method of the invention, e.g., disposables such as pipet tips or vessels to be used as reaction receptacles within the reaction module.

Preferably, the analytical system according to the invention further comprises a control unit for controlling system components.

Such a control unit is described supra in the context of the method according to the invention.

It is to be understood that preferred embodiments described for the suspension container also apply to the method and the analytical system according to the invention.

DETAILED DESCRIPTION OF THE FIGURES

Depicted in FIG. 1 is an example of a suspension container (1) according to the invention as seen from above at an angle. In this embodiment, the container comprises a frame (7) embedding the reservoir (8) containing the suspension of binding particles (not shown). The frame further comprises recesses (9) for placing the container into a device such as a shaker comprising indentations fitting into said recesses. Furthermore, the frame comprises indentations (11) for fixing the container. The reservoir comprises a knob (12) at its outer wall which can also serve for fixation or handling of the suspension container.

Also shown are inclined walls (2) which, on the inner surface of the reservoir, form an elongate groove (3) at the bottom of the container. Said groove, depicted as a dotted line, is located in a straight line below and parallel to openings (5) in the cover (4) of the container, said openings comprising a penetrable septum (10) through which pipets or pipet tips can be introduced into the suspension in the reservoir.

The fill-opening (6) serves for the primary filling of the container with the suspension of binding particles, but is preferably sealed afterwards and not used for retrieval of the suspension in this embodiment.

The flattened corner (18) provides the cassette with a horizontal polarity, such that, e.g., a gripper can recognize in which orientation the container should be inserted in a device or, e.g., placed on a shaker.

Figure 2:
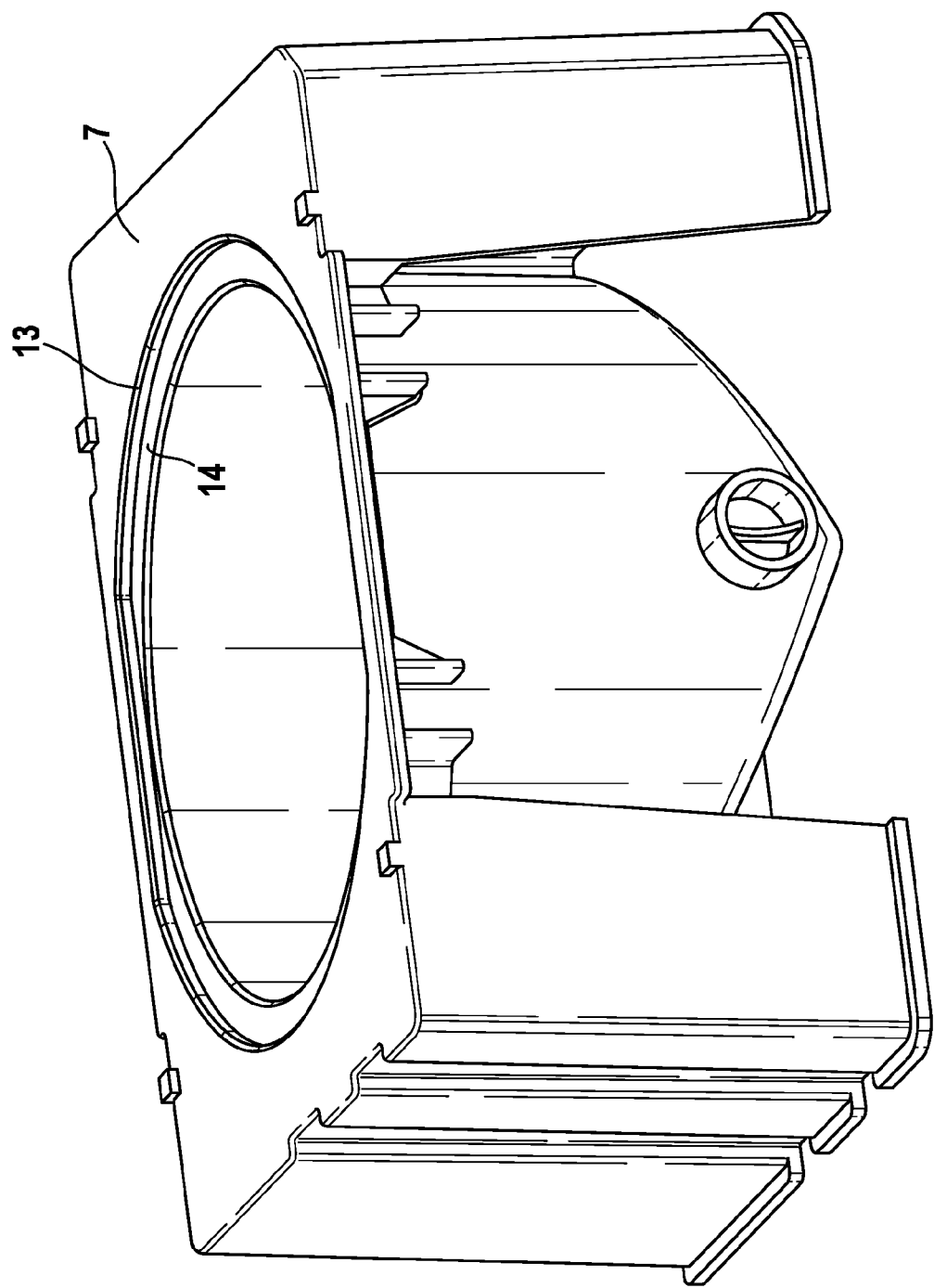
FIG. 2 shows a perspective view of a suspension container without cover from above.

FIG. 2 is a perspective view of a suspension container without cover from above. Even though the cover is part of the suspension container according to the invention, this depiction shows the container without a cover for the sake of clarity. The frame (7) comprises an outer rim (13) and an inner rim (14), wherein the inner rim serves as a rest for supporting the cover (not shown).

Figure 3:
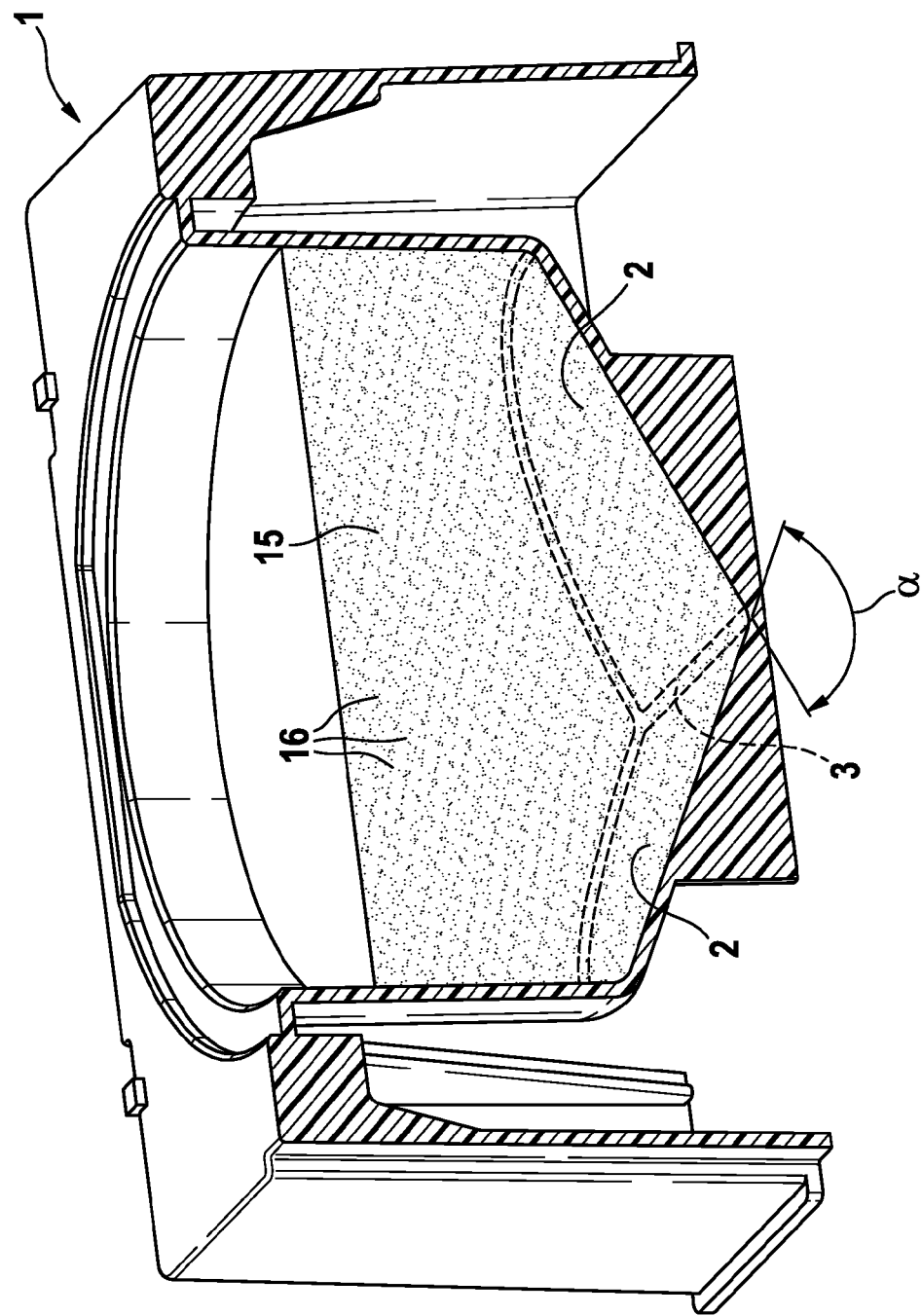
FIG. 3 shows a section view of a suspension container without cover.

This section view in FIG. 3 depicts the interior of the container holding the suspension of binding particles (15). The binding particles (16) are, in this depiction, homogeneously distributed within the fluid matrix. As portions of the suspension are withdrawn from the container, the remainder of the suspension is collected in the elongate groove (3) formed by the inclined inner walls (2), so that the remaining suspension can be quantitatively withdrawn from the container by a linear arrangement of pipets or pipet tips.

Figure 4:
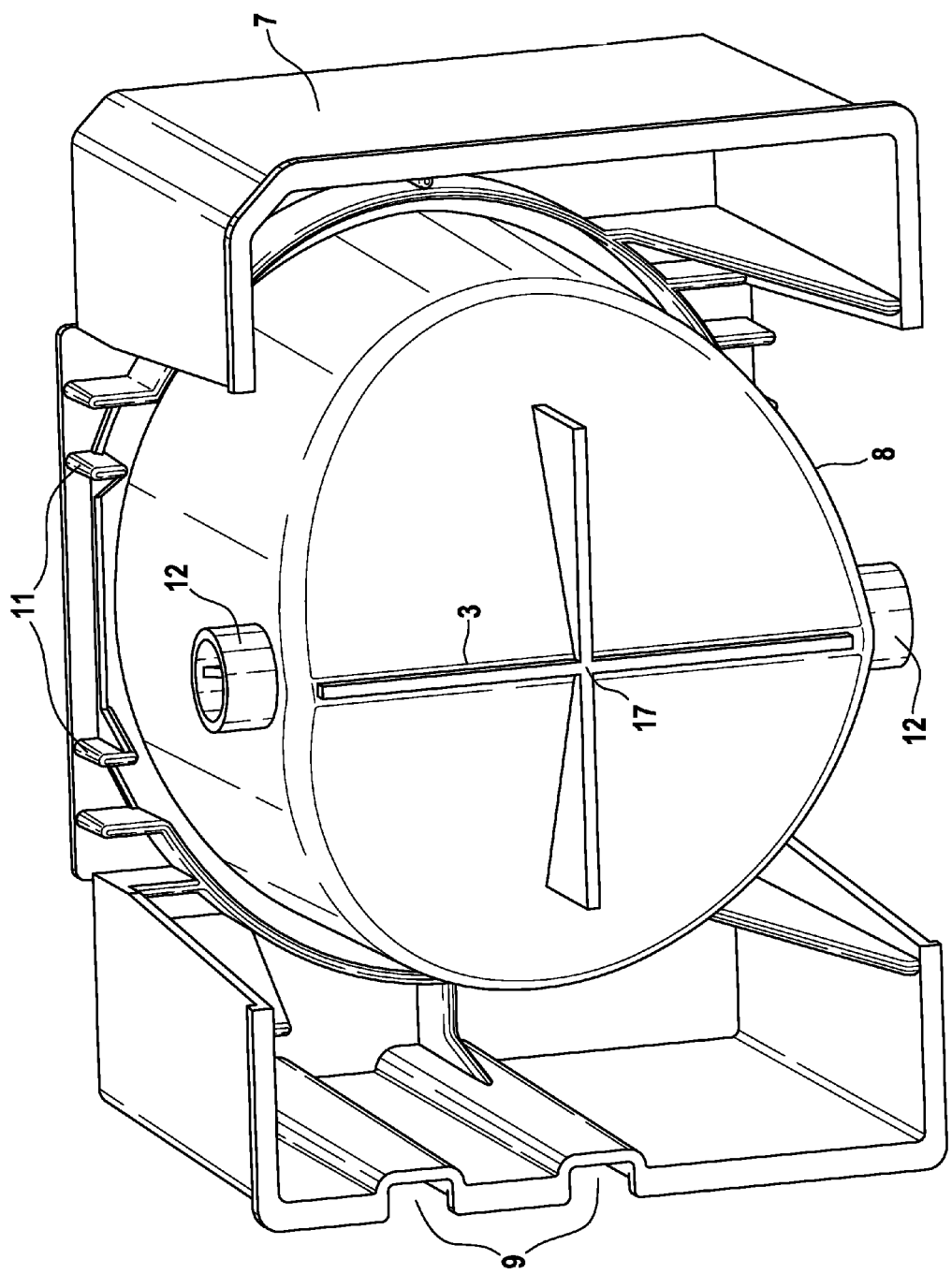
FIG. 4 shows a perspective view of a suspension container from below.

The perspective in FIG. 4 shows the container with the frame (7), the reservoir (8), the recesses (9), indentations (11) and knobs (12) as described above. Further visible from this perspective is a cross-shaped indentation (17), wherein one of the bars is arranged underneath and parallel to the inner groove (3). The cross-shaped indentation is useful, e.g., for mounting the container on a device such as a shaker.

Figure 5:
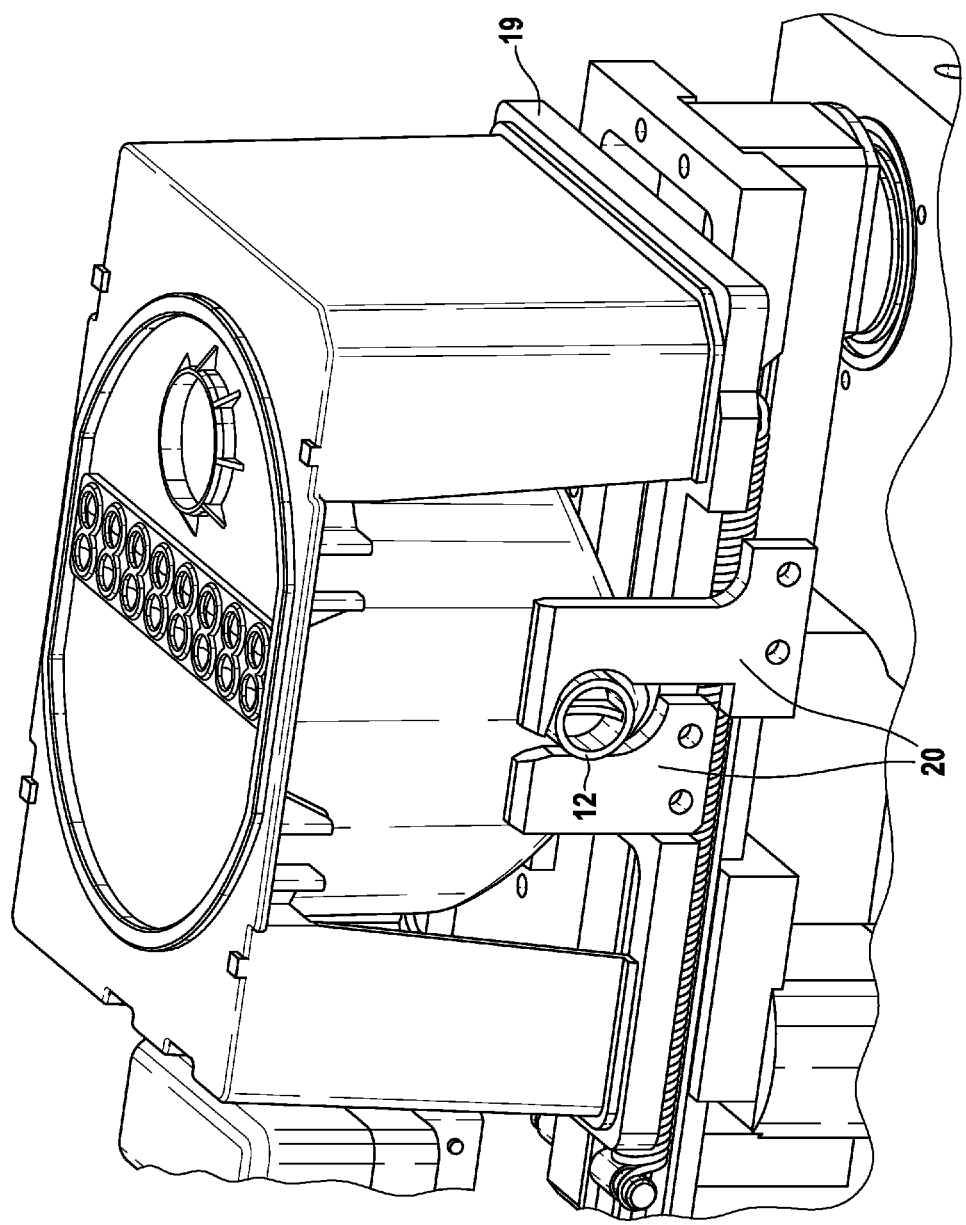
FIG. 5 shows a perspective view of a suspension container placed on a shaking device.

FIG. 5 is a perspective view of a container placed on a shaker (19). It can be seen that the lateral knobs (12) serve to fix the container on said shaker by interaction with a gripping structure on the shaker (20). Depending on the respective movements of the shaker, it can be important that the container is well-fixed. The indentations (9) and (17), visible in FIG. 1 or 4, respectively, can also be useful for fixing the container on the shaker.

Figure 6A:
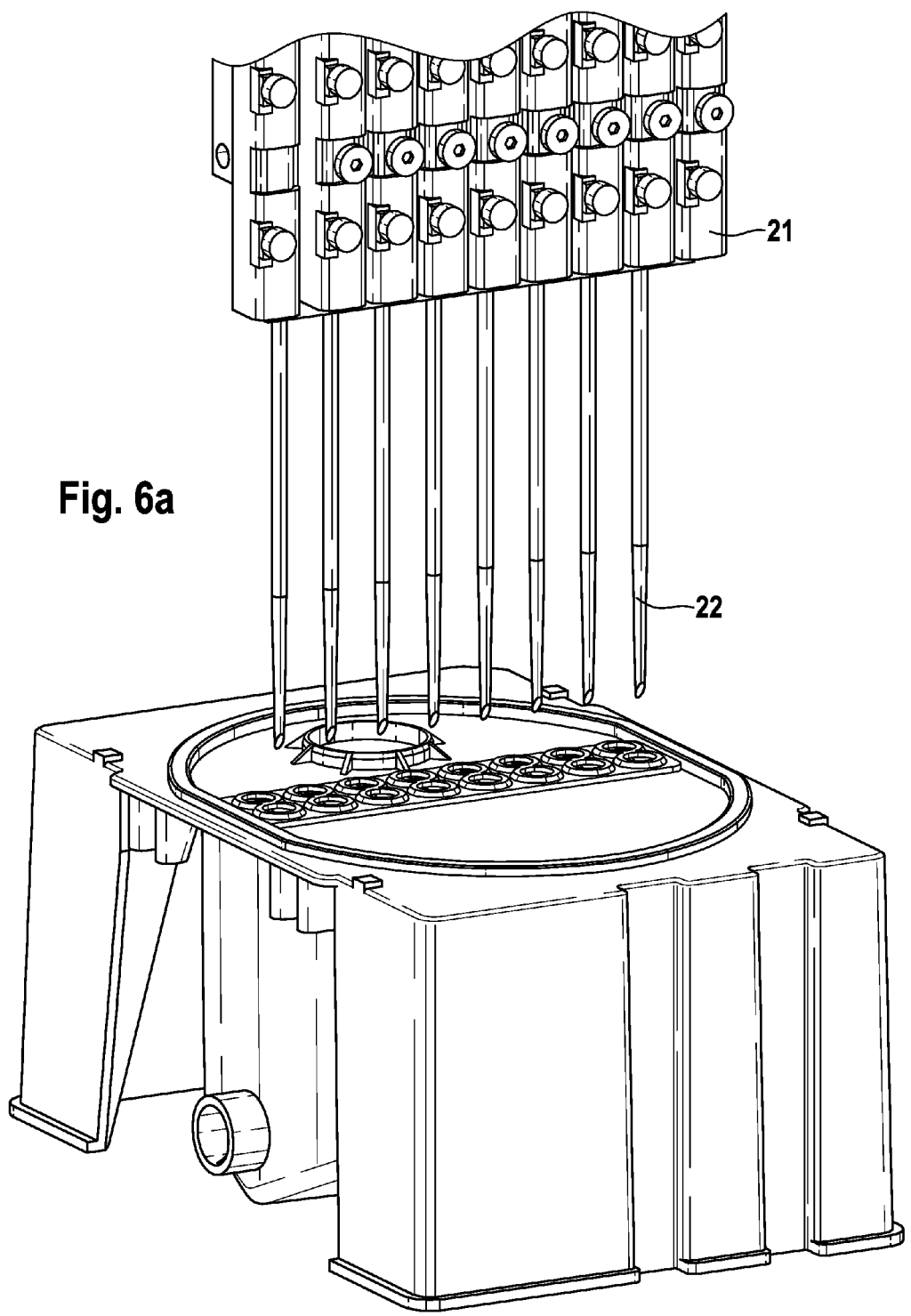
FIGS. 6a-c show a multipipettor interacting with the suspension container.
Figure 6B:
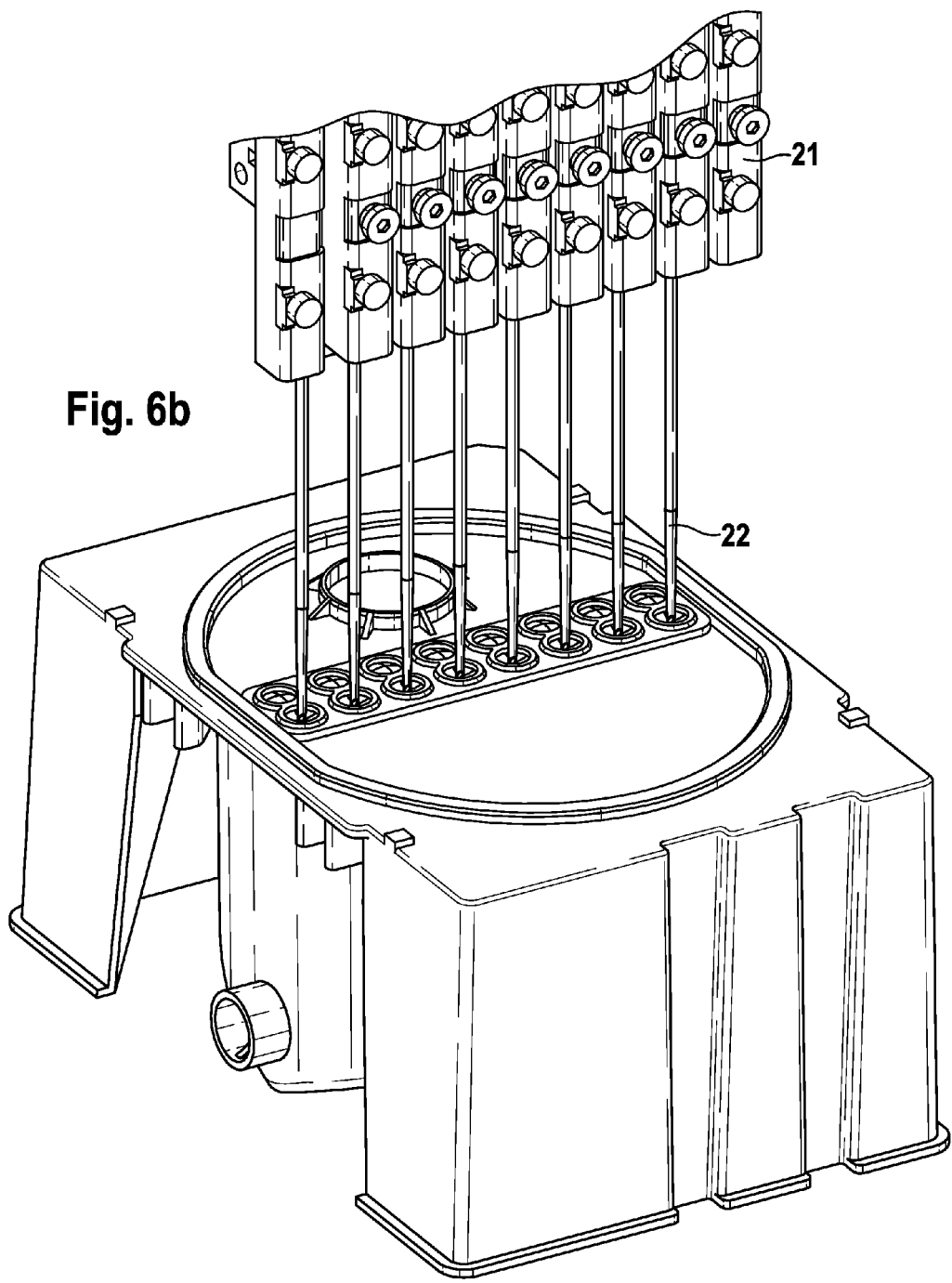
Figure 6C:
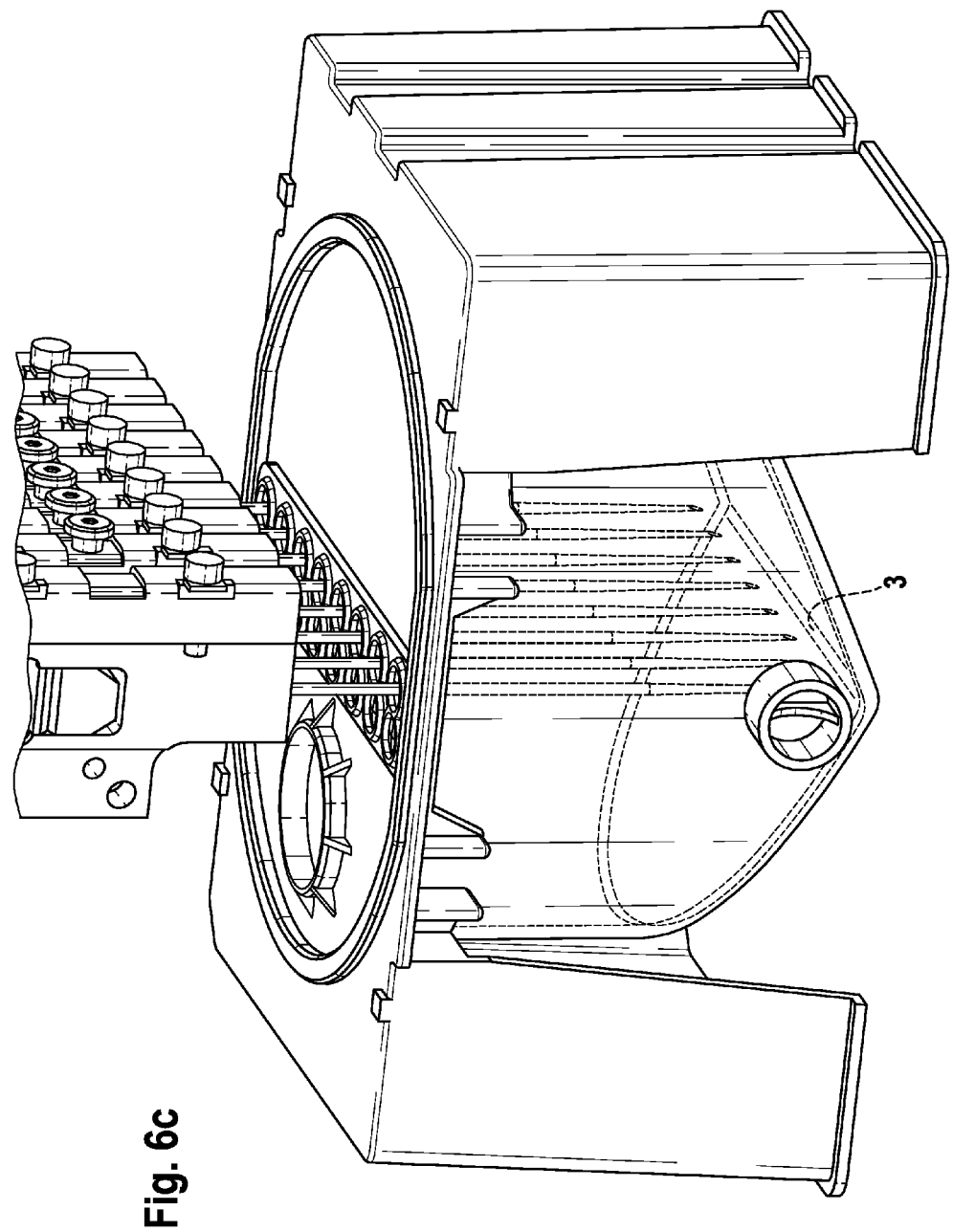

FIG. 6 represents the interaction of the suspension container with a multipipettor (21) comprising pipetting needles (22). In 6a, the needles are placed outside the container in an empty condition. In 6b, the needles are introduced into the container through the cover openings comprising a septum, and in 6c, the pipettor comprising the needles is lowered such far that the needles reach to the elongate groove (3) at the bottom of the container. It is shown that in this embodiment said groove is adapted to the interaction with the depicted multipettor, such that the suspension can be withdrawn in an efficient manner.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed:

1. A method for pipetting a suspension of binding particles for the isolation of biological material, said method comprising the automated steps of:
   agitating a container containing said suspension of binding particles, said container comprising inclined inner walls forming an elongate groove at the bottom of said container positioned along a straight line at the bottom of the container, said container further comprising a cover having openings adapted to receive a linear arrangement of multiple, parallel pipets or pipet tips, wherein said elongate groove is parallel to the openings;
   introducing into said suspension said linear arrangement of multiple, parallel pipets or pipet tips through said openings; and
   aspirating, from the elongate groove, at least a portion of said suspension with a linear arrangement of multiple, parallel pipets or pipet tips and releasing the aspirated suspension or a portion thereof into multiple vessels.

2. The method of claim 1, wherein in said linear arrangement of multiple, parallel pipets or pipet tips simultaneously releases said suspension into said multiple vessels.

3. The method of claim 2, wherein in said linear arrangement of multiple, parallel pipets or pipet tips individually releases said suspension into said multiple vessels by independently manipulating one or more of said multiple, parallel pipets or pipet tips of said linear arrangement.

4. The method of claim 1, wherein said openings comprise a penetrable septum through which pipets or pipet tips can be introduced, said introducing step further comprising penetrating said penetrable septum with said linear arrangement of multiple, parallel pipets or pipet tips.

* * * * *